United States Patent
Yang et al.

(10) Patent No.: US 11,096,876 B2
(45) Date of Patent: *Aug. 24, 2021

(54) DENTIFRICE COMPOSITIONS WITH DUAL FLUORIDE SOURCE WITH IMPROVED FLUORIDE UPDATE

(71) Applicant: The Procter & Gamble Company, Cincinnati, OH (US)

(72) Inventors: Hongmei Yang, Beijing (CN); Haijing Chen, Beijing (CN); Ross Strand, SG (SG)

(73) Assignee: The Procter & Gamble Company, Cincinnati, OH (US)

( * ) Notice: Subject to any disclaimer, the term of this patent is extended or adjusted under 35 U.S.C. 154(b) by 12 days.

This patent is subject to a terminal disclaimer.

(21) Appl. No.: 16/562,472

(22) Filed: Sep. 6, 2019

(65) Prior Publication Data

US 2019/0388312 A1    Dec. 26, 2019

Related U.S. Application Data

(63) Continuation of application No. 15/347,897, filed on Nov. 10, 2016, now Pat. No. 10,463,583.

(51) Int. Cl.

| *A61Q 11/00* | (2006.01) |
| *A61K 8/24* | (2006.01) |
| *A61K 8/19* | (2006.01) |
| *A61K 8/21* | (2006.01) |
| *A61K 8/73* | (2006.01) |
| *A61K 8/25* | (2006.01) |
| *A61K 6/00* | (2020.01) |
| *A61K 8/46* | (2006.01) |

(52) U.S. Cl.
CPC ............. *A61K 8/24* (2013.01); *A61K 8/19* (2013.01); *A61K 8/21* (2013.01); *A61K 8/25* (2013.01); *A61K 8/463* (2013.01); *A61K 8/73* (2013.01); *A61K 8/731* (2013.01); *A61Q 11/00* (2013.01); *A61K 2800/28* (2013.01); *A61K 2800/30* (2013.01); *A61K 2800/48* (2013.01); *A61K 2800/52* (2013.01)

(58) Field of Classification Search
CPC ...... A61Q 11/00; A61K 8/21; A61K 2800/48; A61K 2800/92; A61K 2800/28; A61K 33/16; A61K 2800/30; A61K 8/24; A61K 8/731; A61K 8/25

See application file for complete search history.

(56) References Cited

U.S. PATENT DOCUMENTS

| 3,966,863 A | 6/1976 | Forward |
| 4,046,872 A | 9/1977 | Mitchell |
| 4,138,477 A | 2/1979 | Gaffar |
| 4,144,322 A | 3/1979 | Cordon |
| 4,357,317 A | 11/1982 | Weyn |
| 4,425,323 A | 1/1984 | Morton |
| 4,482,536 A | 11/1984 | Hayes |
| 4,529,584 A | 7/1985 | Mulvey |
| 4,565,691 A | 1/1986 | Jackson |
| 4,678,662 A | 7/1987 | Chan |
| 4,701,319 A | 10/1987 | Woo |
| 4,828,849 A | 5/1989 | Lynch |
| 6,696,045 B2 | 2/2004 | Yue |
| 6,855,325 B1 | 2/2005 | Yvin |
| 8,007,771 B2 | 8/2011 | Ramji |
| 9,364,419 B2 | 6/2016 | Basa |
| 2002/0001569 A1 | 1/2002 | Dromard |
| 2002/0064504 A1 | 5/2002 | Kleinberg |
| 2003/0157033 A1 | 8/2003 | Endo |
| 2004/0120902 A1 | 6/2004 | Wernett |
| 2004/0131560 A1 | 7/2004 | Corcoran |
| 2006/0159631 A1 | 7/2006 | Buch |
| 2007/0053849 A1 | 3/2007 | Doyle |
| 2007/0166243 A1 | 7/2007 | Yoshida |
| 2007/0224134 A1 | 9/2007 | Regner |
| 2007/0231278 A1 | 10/2007 | Lee |
| 2009/0269287 A1 | 10/2009 | Berta |
| 2009/0280072 A1 | 11/2009 | Shiba |
| 2010/0136069 A1 | 6/2010 | Deckner |
| 2010/0247589 A1 | 9/2010 | Fahnestock |
| 2010/0316580 A1 | 12/2010 | Kohli |
| 2012/0251466 A1 | 10/2012 | Pilch |
| 2013/0022427 A1 | 1/2013 | Yamanaka |
| 2013/0064779 A1 | 3/2013 | Yamane |
| 2013/0224270 A1* | 8/2013 | Robinson ................ A61K 8/44 424/401 |
| 2014/9127143 | 5/2014 | Chandrasekaran |
| 2014/0308321 A1 | 10/2014 | Midha |

(Continued)

FOREIGN PATENT DOCUMENTS

| CN | 1216461 A | 5/1999 |
| EP | 0040738 A2 | 12/1981 |

(Continued)

OTHER PUBLICATIONS

PCT Search Report and Written Opinion for PCT/CN2015/094508 dated Nov. 13, 2015.
Ayad et al "Comparing the efficacy in reducing dentin hypersensitivity of a new toothpaste containing 8.0% arginine, calcium carbonate, and 1450 ppm fluoride to a commercial sensitive toothpaste containing 2% potassium ion: an eight-week clinical study on Canadian adults", Journal of Clinical Dentis, Professional Audience Communications, Yardley, PA, v 1. 20, No. 1, Jan. 1, 2009, pp. 10-16.
PCT/CN2015/094504 International Search Report and Written Opinion dated Aug. 9, 2016.
PCT/CN2015/094504 Supplementary International Search Report and Written Opinion dated Dec. 13, 2017.
PCT/CN2015/094505 International Search Report and Written Opinion dated Nov. 13, 2015.

(Continued)

*Primary Examiner* — Tracy Liu
(74) *Attorney, Agent, or Firm* — Parker D. McCrary

(57) ABSTRACT

A dentifrice composition containing water, a calcium-containing abrasive, a sodium monofluorophosphate, and an alkaline metal fluoride were the composition has a high fluoride uptake.

16 Claims, No Drawings

(56) References Cited

U.S. PATENT DOCUMENTS

| | | |
|---|---|---|
| 2014/0356300 A1 | 12/2014 | Morgan |
| 2015/0050322 A1 | 2/2015 | Ashcroft |
| 2015/0328089 A1 | 11/2015 | Chen |
| 2015/0328091 A1 | 11/2015 | Lei |
| 2015/0328093 A1 | 11/2015 | Chen |
| 2015/0328094 A1 | 11/2015 | Xu |
| 2015/0328105 A1 | 11/2015 | Strand |
| 2015/0328131 A1 | 11/2015 | Basa |
| 2015/0352019 A1 | 12/2015 | Chen |
| 2016/0000667 A1 | 1/2016 | Potnis |
| 2016/0030326 A1 | 2/2016 | Basa |
| 2016/0250117 A1 | 9/2016 | Basa |
| 2016/0317406 A1 | 11/2016 | Chen |
| 2017/0014321 A1 | 1/2017 | D'ambrogio |

FOREIGN PATENT DOCUMENTS

| | | |
|---|---|---|
| EP | 0092929 A2 | 11/1983 |
| EP | 0129201 A2 | 12/1984 |
| EP | 0333301 A2 | 9/1989 |
| EP | 3045503 A1 | 7/2016 |
| GB | 1132830 A | 11/1968 |
| GB | 2153673 A | 8/1985 |
| GB | 2188548 A | 10/1987 |
| KR | 20020054045 | 7/2002 |
| KR | 20120042399 A | 5/2012 |
| WO | WO9932074 A2 | 7/1999 |
| WO | WO1999032074 A1 | 7/1999 |
| WO | WO9944571 A1 | 9/1999 |
| WO | WO0245678 A2 | 6/2002 |
| WO | WO03030850 A1 | 4/2003 |
| WO | WO2007122146 A1 | 11/2007 |
| WO | WO2009134657 A1 | 11/2009 |
| WO | WO2011152819 A1 | 12/2011 |
| WO | WO2016172334 A1 | 10/2016 |

OTHER PUBLICATIONS

PCT/CN2015/094505 Supplementary International Search Report and Written Opinion dated Nov. 10, 2017.
PCT/CN2015/094506 International Search Report and Written Opinion for dated Nov. 13, 2015.
PCT/CN2015/094506 Supplementary International Search Report and Written Opinion for dated Oct. 20, 2017.
PCT/CN2015/094508 Supplementary International Search Report and Written Opinion dated Oct. 10, 2017.
PCT/CN2015/094509 International Search Report dated Nov. 13, 2015.
PCT/CN2015/094509 Supplementary International Search Report dated Oct. 10, 2017.
PCT/CN2015/094514 International Search Report dated Nov. 13, 2015.
PCT/CN2015/094514 Supplementary International Search Report dated Oct. 10, 2017.
Pearce, E.I.F. et al., "The Effect of pH, Temperature and Plaque Thickness on the Hydrolysis of Monofluorophosphate in Experimental Dental Plaque", Caries Res. 2003; 37:178-184.
Snorek et al. PQRI Recommendations on Particle-Size Analysis of Drug Substances Used in Oral Dosage Forms. Jun. 2007. J Pharm Sci. vol. 96. No. 6. pp. 1451-1467.
Xu, Pengcheng, "Effect of arginine dentifrice on remineralization of initial enamel carious lesions" West China Journal of Stomatology, Feb. 28, 2014, No. 1, vol. 32.
Zhao, Yinfa et al. "Yagao Yong Tansuangai Lidu Pingjia" Toothpaste Industry 30 Apr. 4, 2007, No. 2, vol. 2007.
All Office Actions, U.S. Appl. No. 15/347,823.
All Office Actions, U.S. Appl. No. 15/347,824.
All Office Actions, U.S. Appl. No. 15/347,840.
All Office Actions, U.S. Appl. No. 15/347,830.
All Office Actions, U.S. Appl. No. 15/347,837.
All Office Actions, U.S. Appl. No. 15/347,821.
All Office Actions, U.S. Appl. No. 15/347,897.

* cited by examiner

DENTIFRICE COMPOSITIONS WITH DUAL FLUORIDE SOURCE WITH IMPROVED FLUORIDE UPDATE

FIELD OF THE INVENTION

The present invention relates to dentifrice compositions having improved fluoride uptake.

BACKGROUND OF THE INVENTION

Dentifrice compositions are well known for dental and oral hygiene care. High water (e.g., >44 wt %) and high carbonate (e.g., >24 wt %) formulation chassis are cost effective for many markets and consumers. Dental plaque is a sticky, colorless deposit of bacteria that is constantly forming on the tooth surface. Saliva, food and fluids combine to produce these deposits that collect where the teeth and gums meet. Plaque buildup is the primary factor in poor oral health that can lead to caries and periodontal (gum) disease, including gingivitis. One way dentifrice compositions help prevent and control plaque is by leveraging anti-bacterial agents; however, the disadvantage and formulation challenge is the unintended reactivity of anti-bacterial agents with formulation ingredients and environment of containing calcium carbonate matrix. This may include oxidative degradation, hydrolysis, adsorption or precipitation of oxy-hydroxide species, any of which can impact the bio-availability of the anti-bacterial agent. There is a continuing need to provide such formulations that help prevent plaque formation on teeth and/or minimize the use of antimicrobial agents, particularly in high water and high carbonate dentifrice formulation chassis.

SUMMARY OF THE INVENTION

A surprising discovery is the role of pH in high water and high carbonate dentifrice formulations. Specifically, an alkaline pH, i.e., higher than 7.8, preferably higher than pH 8, contributes to anti-plaque or plaque mitigation benefits to the dentifrice compositions described herein. The alkaline pH helps to provide an inhospitable environment for many types of bacteria. Yet furthermore, the dentifrice formulations containing a dual fluoride source, specifically sodium monofluorophosphate and alkaline metal fluoride, provide superior fluoride uptake results.

One aspect of the invention provides for a dentifrice composition comprising: 45% to 75%, by weight of the composition, of water; 25% to 50%, by weight of the composition, of a calcium-containing abrasive; 0.0025% to 2%, by weight of the composition, of a sodium monofluorophosphate; 0.0025% to 2%, by weight of the composition, of an alkaline metal fluoride; and a pH greater than 7.8.

Yet another aspect of the invention provides a method of treating tooth enamel comprising the step of brushing teeth with a dentifrice composition of the present invention.

Yet still another aspect of the invention provides a method preventing or mitigating plaque formation on tooth enamel comprising the step of brushing teeth with a dentifrice composition of the present invention.

These and other features, aspects, and advantages of the present invention will become evident to those skilled in the art from the detailed description which follows.

DETAILED DESCRIPTION OF THE INVENTION

Definitions

The term "comprising" as used herein means that steps and ingredients other than those specifically mentioned can be added. This term encompasses the terms "consisting of" and "consisting essentially of." The compositions of the present invention can comprise, consist of, and consist essentially of the essential elements and limitations of the invention described herein, as well as any of the additional or optional ingredients, components, steps, or limitations described herein.

The term "dentifrice" as used herein means paste, gel, powder, tablets, or liquid formulations, unless otherwise specified, that are used to clean the surfaces of the oral cavity. Preferably the dentifrice compositions of the present invention are single phase compositions. The term "teeth" as used herein refers to natural teeth as well as artificial teeth or dental prosthesis.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified. The term "weight percent" may be denoted as "wt %" herein. All molecular weights as used herein are weight average molecular weights expressed as grams/mole, unless otherwise specified.

As used herein, the articles including "a" and "an" when used in a claim, are understood to mean one or more of what is claimed or described.

As used herein, the terms "comprise", "comprises", "comprising", "include", "includes", "including", "contain", "contains", and "containing" are meant to be non-limiting, i.e., other steps and other sections which do not affect the end of result can be added. The above terms encompass the terms "consisting of" and "consisting essentially of".

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

Water

The dentifrice compositions of the present invention comprise herein from 45% to 75%, by weight of the composition, of water. Preferably, the dentifrice composition comprises from 45% to 65%, more preferably from 45% to 55%, yet more preferably from 46% to 54%, by weight of the composition, of water. The water may be added to the formulation and/or may come into the composition from the inclusion of other ingredients. Preferably the water is USP water.

Calcium-Containing Abrasive

The compositions of the present invention comprise from 25% to 50%, by weight of the composition, of a calcium-containing abrasive, wherein preferably the calcium-containing abrasive is selected from the group consisting of calcium carbonate, calcium glycerophosphate, dicalcium phosphate, tricalcium phosphate, calcium orthophosphate, calcium metaphosphate, calcium polyphosphate, calcium oxyapatite, sodium carbonate, and combinations thereof. Preferably, the composition comprises from 27% to 47%, more preferably from 27% to 37%, even more preferably from 28% to 34%, yet even more preferably from 29% to 33%, by weight of the composition, alternatively combinations thereof, of a calcium-containing abrasive.

Preferably, the calcium-containing abrasive is calcium carbonate. More preferably, the calcium-containing abrasive is selected from the group consisting of fine ground natural chalk, ground calcium carbonate, precipitated calcium carbonate, and combinations thereof.

Fine ground natural chalk (FGNC) is one of the more preferred calcium-containing abrasives useful in the present invention. It is obtained from limestone or marble. FGNC may also be modified chemically or physically by coating during milling or after milling by heat treatment. Typical coating materials include magnesium stearate or oleate. The morphology of FGNC may also be modified during the milling process by using different milling techniques, for example, ball milling, air-classifier milling or spiral jet milling. One example of natural chalk is described in WO 03/030850 having a medium particle size of 1 to 15 μm and a BET surface area of 0.5 to 3 $m^2/g$. The natural calcium carbonate may have a particle size of 325 to 800 mesh, alternatively a mess selected from 325, 400 600, 800, or combinations thereof; alternatively, the particle size is from 0.1 to 30 microns, or from 0.1 to 20 microns, or from 5 to 20 microns. In one embodiment, the composition comprises from 0% to 5%, preferably 0% to 3%, more preferably 0% to 1%, by weight of the composition, of a silicate; yet more preferably the composition is substantially free silicate.

Dual Fluoride Ion Source

The dentifrice compositions of the present invention notably have a dual fluoride ion source, specifically sodium monofluorophosphate and an alkaline metal fluoride. Levels of these fluoride ion sources include: 0.0025% to 2%, by weight of the composition, of a sodium monofluorophosphate, and 0.0025% to 2%, by weight of the composition, of an alkaline metal fluoride. Preferably, the dentifrice composition comprises from 0.2% to 1.5%, more preferably from 0.5% to 1%, yet more preferably from 0.6% to 0.9%, by weight of the composition, of the sodium monofluorophosphate. Preferably, the dentifrice composition comprises from 0.01% to 0.3%, preferably from 0.01% to 0.2%, more preferably from 0.05% to 0.15%, by weight of the composition, of the alkaline metal fluoride. Preferably, the alkaline metal fluoride is potassium fluoride, sodium fluoride, more preferably sodium fluoride.

pH

The pH of the dentifrice composition may be greater than pH 7.8, preferably greater than pH 8, more preferably from greater than pH 8.0 to pH 11. Preferably, the pH is greater than 8.1, more preferably the pH is greater than pH 8.5, even more preferably the pH is greater than pH 9, alternatively the pH is from pH 9.0 to pH 10.5, alternatively from pH 9 to pH 10. The relatively high pH of the present inventive composition is for fluoride stability. Without wishing to be bound theory, at below pH 8 calcium ion may bind with the fluoride. Thus, it is desirable to have the dentifrice composition have a greater than pH 8.0 to maximize the stability of the fluoride ion source. A method for assessing pH of dentifrice is described is provided the analytical methods section provided below. For purposes of clarification, although the analytical method describes testing the dentifrice composition when freshly prepared, for purposes of claiming the present invention, the pH may be taken at anytime during the product's reasonable lifecycle (including but not limited to the time the product is purchased from a store and brought to the consumer's home).

pH Modifying Agent

The dentifrice compositions herein may include an effective amount of a pH modifying agent, alternatively wherein the pH modifying agent is a pH buffering agent. The pH modifying agents, as used herein, refer to agents that can be used to adjust the pH of the dentifrice compositions to the above-identified pH range. The pH modifying agents may include alkali metal hydroxides, ammonium hydroxide, organic ammonium compounds, carbonates, sesquicarbonates, borates, silicates, phosphates, imidazole, and mixtures thereof. Specific pH agents include monosodium phosphate (monobasic sodium phosphate or "MSP"), trisodium phosphate (sodium phosphate tribasic dodecahydrate or "TSP"), sodium benzoate, benzoic acid, sodium hydroxide, potassium hydroxide, alkali metal carbonate salts, sodium carbonate, imidazole, pyrophosphate salts, sodium gluconate, lactic acid, sodium lactate, citric acid, sodium citrate, phosphoric acid. In one embodiment, 0.01% to 3%, preferably from 0.1% to 1%, by weight of the composition, of TSP, and 0.001% to 2%, preferably from 0.01% to 0.3%, by weight of the composition, of monosodium phosphate is used. Without wishing to be bound by theory, TSP and monosodium phosphate may also have calcium ion chelating activity and therefore provide some monofluorophosphate stabilization (in those formulations containing monofluorophosphate).

A method for assessing pH of dentifrice is described. The pH is measured by a pH Meter with Automatic Temperature Compensating (ATC) probe. The pH Meter is capable of reading to 0.001 pH unit. The pH electrode may be selected from one of the following (i) Orion Ross Sure-Flow combination: Glass body—VWR #34104-834/Orion #8172BN or VWR #10010-772/Orion #8172BNWP; Epoxy body—VWR #34104-830/Orion #8165BN or VWR #10010-770/Orion #8165BNWP; Semi-micro, epoxy body—VWR #34104-837/Orion #8175BN or VWR #10010-774/Orion #3175BNWP; or (ii) Orion PerpHect combination: VWR #34104-843/Orion #8203BN semi-micro, glass body; or (iii) suitable equivalent. The automatic temperature compensating probe is Fisher Scientific, Cat #13-620-16.

A 25% by weight slurry of dentifrice is prepared with deionized water, and thereafter is centrifuged for 10 minutes at 15000 rotations-per-minute using a SORVALL RC 28S centrifuge and SS-34 rotor (or equivalent gravitational force, at 24149 g force). The pH is assessed in supernatant after one minute or the taking reading is stabilized. After each pH assessment, the electrode is washed with deionized water. Any excess water is wiped with a laboratory grade tissue. When not in issue, the electrode is kept immersed in a pH 7 buffer solution or an appropriate electrode storage solution.

Thickening System

The dentifrice compositions of the present invention may comprise a thickening system. Preferably the dentifrice composition comprises from 0.5% to 4%, preferably from 0.8% to 3.5%, more preferably from 1% to 3%, yet still more preferably from 1.3% to 2.6%, by weight of the composition, of the thickening system. More preferably the thickening system comprises a thickening polymer, a thickening silica, or a combination thereof. Yet more preferably, when the thickening system comprises a thickening polymer, the thickening polymer is selected from a carboxymethyl cellulose, a linear sulfated polysaccharide, a natural gum, and combination thereof. Yet still more preferably, when the thickening system comprises a thickening polymer, the thickening polymer is selected from the group consisting of: (a) 0.01% to 3% of a carboxymethyl cellulose ("CMC") by weight of the composition, preferably 0.1% to 2.5%, more preferably 0.2% to 1.5%, by weight of the composition, of CMC; (b) 0.01% to 2.5%, preferably 0.05% to 2%, more preferably 0.1% to 1.5%, by weight of the composition, of a linear sulfated polysaccharide, preferably wherein the linear sulfated polysaccharide is a carrageenan; (c) 0.01% to 7%, preferably 0.1% to 4%, more preferably from 0.1% to 2%, yet more preferably from 0.2% to 1.8%, by weight of the composition, of a natural gum; (d) combinations thereof. Preferably when the thickening system comprises a thickening silica, the thickening silica is from 0.01% to 10%, more preferably from 0.1% to 9%, yet more preferably 1% to 8% by weight of the composition.

Preferably the linear sulfated polysaccharide is a carrageenan (also known as carrageenin). Examples of carrageenan include Kappa-carrageenan, Iota-carrageenan, Lambda-carrageenan, and combinations thereof.

In one example the thickening silica is obtained from sodium silicate solution by destabilizing with acid as to yield very fine particles. One commercially available example is ZEODENT® branded silicas from Huber Engineered Materials (e.g., ZEODENT® 103, 124, 113 115, 163, 165, 167).

In one example the CMC is prepared from cellulose by treatment with alkali and monochloro-acetic acid or its sodium salt. Different varieties are commercially characterized by viscosity. One commercially available example is Aqualon™ branded CMC from Ashland Special Ingredients (e.g., Aqualon™ 7H3SF; Aqualon™ 9M3SF Aqualon™ TM9A; Aqualon™ TM12A).

Preferably a natural gum is selected from the group consisting of gum karaya, gum arabic (also known as acacia gum), gum tragacanth, xanthan gum, and combination thereof. More preferably the natural gum is xanthan gum. Xanthan gum is a polysaccharide secreted by the bacterium *Xanthomonas camestris*. Generally, xanthan gum is composed of a pentasaccharide repeat units, comprising glucose, mannose, and glucuronic acid in a molar ratio of 2:2:1, respectively. The chemical formula (of the monomer) is $C_{35}H_{49}O_{29}$. In one example, the xanthan gum is from CP Kelco Inc (Okmulgee, US).

Viscosity

Preferably the dentifrice compositions of the present invention have a viscosity range from 150,000 centipoise to 850,000 centipoise ("cP"). A method for assessing viscosity is described. The viscometer is Brookfield® viscometer, Model DV-I Prime with a Brookfield "Helipath" stand. The viscometer is placed on the Helipath stand and leveled via spirit levels. The E spindle is attached, and the viscometer is set to 2.5 RPM. Detach the spindle, zero the viscometer and install the E spindle. Then, lower the spindle until the crosspiece is partially submerged in the paste before starting the measurement. Simultaneously turn on the power switch on the viscometer and the helipath to start rotation of the spindle downward. Set a timer for 48 seconds and turn the timer on at the same time as the motor and helipath. Take a reading after the 48 seconds. The reading is in cP.

PEG

The compositions of the present invention may optionally comprise polyethylene glycol (PEG), of various weight percentages of the composition as well as various ranges of average molecular weights. In one aspect of the invention, the compositions have from 0.01% to 8%, preferably from 0.1% to 5%, more preferably from 0.2% to 4.8%, yet more preferably from 0.3% to 4.2%, yet still more preferably from 0.5% to 4%, by weight of the composition, of PEG. In another aspect of the invention, the PEG is one having a range of average molecular weight from 100 Daltons to 1600 Daltons, preferably from 200 to 1000, alternatively from 400 to 800, alternatively from 500 to 700 Daltons, alternatively combinations thereof. PEG is a water soluble linear polymer formed by the addition reaction of ethylene oxide to an ethylene glycol equivalent having the general formula is: $H-(OCH_2CH_2)_n-OH$. One supplier of PEG is Dow Chemical Company under the brandname of CARBOWAX™. Without wishing to be bound by theory, having some PEG in the dentifrice composition may help with physical stability.

Sweetener

The oral care compositions herein may include a sweetening agent. These include sweetening agents may include saccharin, dextrose, sucrose, lactose, maltose, levulose, aspartame, sodium cyclamate, D-tryptophan, dihydrochalcones, acesulfame, sucralose, neotame, and mixtures thereof. Sweetening agents are generally used in oral compositions at levels of from 0.005% to 5%, by weight of the composition, alternatively 0.01% to 1%, alternatively from 0.1% to 0.5%, alternatively combinations thereof.

Anti-Calculus Agent

The dentifrice compositions may include an effective amount of an anti-calculus agent, which in one embodiment may be present from 0.05% to 50%, by weight of the composition, alternatively from 0.05% to 25%, alternatively from 0.1% to 15% by weight of the composition. Non-limiting examples include those described in US 2011/0104081 A1 at paragraph 64, and those described in US 2012/0014883 A1 at paragraphs 63 to 68, as well as the references cited therein. One example is a pyrophosphate salt as a source of pyrophosphate ion. In one embodiment, the composition comprises tetrasodium pyrophosphate (TSPP) or disodium pyrophosphate or combinations thereof, preferably 0.01% to 2%, more preferably from 0.1% to 1%, by weight of the composition, of the pyrophosphate salt. Without wishing to be bound by theory, TSPP may provide not only calcium chelating thereby mitigating plaque formation, but also may also provide the additional benefit of monofluorophosphate stabilization (in those formulations containing monofluorophosphate).

Surfactant

The dentifrice compositions herein may include a surfactant. The surfactant may be selected from anionic, nonionic, amphoteric, zwitterionic, cationic surfactants, or mixtures thereof. The composition may include a surfactant at a level of from 0.1% to 10%, from 0.025% to 9%, from 0.05% to 5%, from 0.1% to 2.5%, from 0.5% to 2%, or from 0.1% to 1% by weight of the total composition. Non-limiting examples of anionic surfactants may include those described at US 2012/0082630 A1 at paragraphs 32, 33, 34, and 35. Non-limiting examples of zwitterionic or amphoteric surfactants may include those described at US 2012/0082630 A1 at paragraph 36; cationic surfactants may include those described at paragraphs 37 of the reference; and nonionic surfactants may include those described at paragraph 38 of the reference. In one embodiment the composition comprises 0.1% to 5%, preferably 0.1% to 3%, alternatively from 0.3% to 3%, alternatively from 1.2% to 2.4%, alternatively from 1.2% to 1.8%, alternatively from 1.5% to 1.8%, by weight of the composition, alternatively combinations thereof, of the anionic surfactant sodium lauryl sulfate (SLS).

Low Level or Free of Humectants

The compositions herein may be substantially free or free of humectants, alternatively contain low levels of humectants. The term "humectant," for the purposes of present invention, include edible polyhydric alcohols such as glycerin, sorbitol, xylitol, butylene glycol, propylene glycol, and combinations thereof. In one embodiment, the humectant is a polyol, preferably wherein the polyol is selected from sorbitol, glycerin, and combinations thereof. In yet another embodiment, the humectant is sorbitol. In one embodiment, the composition comprises from 0% to less than 5%, by weight of the composition, of humectants, preferably from 0% to 4%, alternatively from 0% to 3%, alternatively from 0% to 2%, alternatively from 0% to 1%, by weight of humectants by weight of the composition. A potential advantage of having a dentifrice composition that is free or substantially free of humectants is, without wishing to be bound by theory, is those dentifrice compositions that are free of polyols (e.g., glycerin and sorbitol), or have a relatively low amount thereof, may provide better fluoride uptake compared to those compositions having the high levels of such polyols (or humectants for that matter). In one example, the dentifrice compositions of the present invention comprise from 0% to 5%, preferably 0% to 3%, more preferably 0% to 1%, by weight of the composition, of glycerin, sorbitol, or combinations thereof; yet more preferably the composition is substantially free of both glycerin and sorbitol.

Colorant

The compositions herein may include a colorant. Titanium dioxide is one example of a colorant. Titanium dioxide is a white powder which adds opacity to the compositions. Titanium dioxide generally can comprise from 0.25% to 5%, by weight of the composition.

Flavorant

The compositions herein may include from 0.001% to 5%, alternatively from 0.01% to 4%, alternatively from 0.1% to 3%, alternatively from 0.5% to 2%, alternatively 1% to 1.5%, alternatively 0.5% to 1%, by weight of the composition, alternatively combinations thereof, of a flavorant composition. The term flavorant composition is used in the broadest sense to include flavor ingredients, or sensates, or sensate agents, or combinations thereof. Flavor ingredients may include those described in US 2012/0082630 A1 at paragraph 39; and sensates and sensate ingredients may include those described at paragraphs 40-45, incorporated herein by reference. Excluded from the definition of flavorant composition is "sweetener" (as described above).

Examples

Fluoride uptake in dental plaque is an important metric in assessing the efficacy of anti-plaque or plaque mitigation benefits of the dentifrice compositions described herein. Fluoride is known to have the potential to exert an anti-caries benefit largely through three mechanisms; inhibition of demineralization, promotion of remineralization and interference with bacterial growth and metabolism. Small but protracted elevations in fluoride levels are linked to modification of the demineralization/remineralization balance by direct effects on the dental mineral. Plaque fluoride levels have been clinically correlated with dose response in providing anti-caries. Thus the fluoride pharmacokinetic reservoirs and the bioavailability of fluoride in saliva, and consequently in plaque fluid, play a crucial role in preventing a net mineral deficit. The source of the fluoride can also play an important role as the source used will lead to different salivary fluoride concentrations post brushing. Sodium fluoride (Na—F) is instantly dissociated in saliva, whereas, sodium monofluorophosphate (Na-MFP) requires hydrolysis to release free fluoride ions. The different dissolution properties can lead to different fluoride concentrations in plaque, consequently affecting the caries protective effect of plaque fluoride content. The fluoride binding to the plaque reservoirs and the release from the reservoir is a complex multi-mechanism; binding to the anionic sites on the bacterial wall, within the plaque matrix constituents via calcium bridging, binding to calcification nuclei or diffusion kinetics based on the specific plaque matrix.

Improved Fluoride Uptake in Dual Fluoride Source/High Water/High Carbonate Dentifrice Compositions Data is provided to demonstrate the superiority of inventive Example 1 in fluoride uptake. The dual fluoride source, nil polyol humectant, at pH 9.5 dentifrice formulation of example 1 provides better results as compared to comparative examples 2 and 3, as well as control compositions that include marketed toothpaste products. Table 1 below details the components of the five compositions on a weight percentage (wt %) basis. Methods are described including determining Mean Fluoride Uptake. Lastly, data is presented in Table 2.

Compositional Components

TABLE 1

Compositional components of inventive example 1, comparative examples 2 and 3, and control compositions A and B.

| Components: (Wt %) | Ex 1 (Inventive) Dual Fluoride Source | Ex 2 Single Fluoride Source | Ex 3 Single Fluoride and Humectant | Control A Single Fluoride | Control B Single Fluoride |
|---|---|---|---|---|---|
| Water | 59 | 58.7 | 31 | 98.9 | 98 |
| CaCO$_3$ | 32 | 32 | 42 | 0 | 0 |
| Sodium Monofluorophosphate ("Na-MFP") | 0.76 | 1.1 | 1.1 | 0 | 0 |
| Sodium Fluoride ("Na—F") | 0.1 | 0 | 0 | 0.32 | 0.62 |
| Glycerin | 0 | 0 | 0 | 0 | 0 |
| Sorbitol | 0 | 0 | 17 | 0 | 0 |
| Sodium Caboxymethyl Cellulose | 0.9 | 0.9 | 1.3 | 0 | 0 |
| Carrageenan | 1.2 | 1.2 | 0 | 0 | 0 |
| Thickener Silica | 2.6 | 2.6 | 3 | 0 | 0 |
| Sodium Lauryl Sulfate | 1 | 1 | 2 | 0 | 0 |
| Tetra Sodium Pyrophosphate | 0.6 | 0.6 | 0 | 0 | 0 |
| Flavor | 1 | 1 | 1 | 0 | 0 |

TABLE 1-continued

Compositional components of inventive example 1, comparative examples 2 and 3, and control compositions A and B.

| Components: (Wt %) | Ex 1 (Inventive) Dual Fluoride Source | Ex 2 Single Fluoride Source | Ex 3 Single Fluoride and Humectant | Control A Single Fluoride | Control B Single Fluoride |
|---|---|---|---|---|---|
| Sodium Mono-phosphate | 0.1 | 0.1 | 0.1 | 0 | 0 |
| Sodium Triphosphate | 0.4 | 0.4 | 0.4 | 0 | 0 |
| Sodium Saccharine | 0.25 | 0.25 | 0.25 | 0 | 0 |
| Methyl Paraben | 0.05 | 0.05 | 0 | 0 | 0 |
| Propyl Paraben | 0.05 | 0.05 | 0 | 0 | 0 |
| Total: | 100 | 100 | 100 | 100 | 100 |
| pH: | 9.5 | 9.5 | 8.8 | 8 | 8 |

Referring to Table 1, the inventive composition (Ex 1) notably contains a dual fluoride source system of 0.76 wt % of sodium monofluorophosphate (Na-MFP) and 0.1 wt % of a sodium fluoride (Na—F); nil polyol humectant (i.e., nil glycerin and nil sorbitol); and is at pH 9.5. Example 1 also has a relatively high level of water (59 wt %) and carbonate (32 wt %). Comparative examples 2 and 3 also at a relatively high pH (9.5 and 8.9) and contain relatively high level of water and carbonate, but are only have a single source of fluorides at 1.1 wt % Na-MFP. This level is higher than the inventive composition. Example 3 also has the polyol humectants sorbitol (17 wt %). Control A and Control B both have a single fluoride source of Na—F (at 0.32 wt % and 0.62 wt %, respectively) and both have a pH of 8. Notably, Control B is a clinically proven positive control (internal unpublished data).

Analytical Methods

The method for assessing "Mean Fluoride Uptake" is described. Glass rods (Tianjin Hope Biotech Co., Ltd.) are polished with fine wet/dry #600 sandpaper on lathe. Rods are weighed on a four decimal place balance (Sartorius, BP210 S). Then the rods are mounted on stainless steel racks using rubber o-rings to secure using spacers to control depth.

Culture medium is prepared and autoclaved with 60 g TSB (Becton, Dickinson and Company), 60 G sucrose (Becton, Dickinson and Company), and 2000 ml DI water. 180 ml pooled fresh saliva is mixed with 120 ml Sucrose/TSB solution to form a culture mixture. 7 ml of this mixture is pipetted with repeater pipette into 16×100 mm borosilicate tubes placed in a dosing rack. Glass rod rack and dosing solution rack are placed in incubator overnight with dipping motor on. The mix and growth steps are repeated in the morning and afternoon, and then are incubated overnight. The culture mixture is changed for a total of five times.

Dentifrice treatment is prepared by thoroughly mixing 15 g of dentifrice with 45 g of fresh pooled saliva (i.e., a 1:3 weight ratio). Plaque rods for are dipped for two minutes in ten ml of slurry, and then the rods are rinsed for ten seconds in DI water. This is repeated for a total of two rinses. The treatment is repeated for two minutes and rinsed twice.

A small spatula is sterilized with 70% alcohol. Plaque rods are carefully inserted into sterile labeled, pre-weighed 1.5 ml Eppendorf® tubes and wiped on the sides of the tube. The plaque is dried in the Eppendorf™ tubes in 60° C. incubator overnight until dry. The dried plaque is weighed in the Eppendorf™ tubes on a four decimal place balance. The net plaque weight is calculated. 10 ul of 1.0 M perchloric acid is added to the Eppendorf™ tube. The tubes incubate at room temperature in the hood overnight. In the morning, 100 ml 1.0M NaOH is added to increase the pH to 5.0.

Fluoride concentration is determined from a calibration curve obtained on the same day as the analysis. This standard curve is made using an ion selective electrode (Orion, Model 9609BNWP) and previously made fluoride standards. These standards are made using 1.0 mL fluoride standard and 1.0 mL TISAB II (1:1). The following parts per million ("ppm") F standards are used: 250, 100, 50, 25, 10, 5, 2.5, 1.0, 0.5, 0.1, 0.05, 0.025 and 0.01 ppm F. The equation for log ppm F is then obtained by graphing log ppm F vs. Rel mV readings for each of the above standards and obtaining a linear fit line and equation. In the Eppendorf™ tube, 200 ul of TISAB II buffer is added and allowed to sit for 10 minutes to buffer pH; thereafter, fluoride is measured with an ion selective electrode, calibrated against the standard curve. The data is provided in Table 2 below.

Data

TABLE 2

Mean Fluoride Uptake in Plaque among various dentifrice products/formulations

| Product | pH | Humectant | MFP Ion (ppm) | F Ion (ppm) | Soluble F (ppm) | Fluoride Source (ppm) | Plaque Mean Fluoride Uptake ± (SEM) | Statistic |
|---|---|---|---|---|---|---|---|---|
| Ex 1 | 9.5 | Nil | 4340 | 563 | 1246 | 1450 total fluoride (0.76 wt % Na-MFP, 0.1 wt % Na—F) | 1141 | A |

TABLE 2-continued

Mean Fluoride Uptake in Plaque among various dentifrice products/formulations

| Product | pH | Humectant | MFP Ion (ppm) | F Ion (ppm) | Soluble F (ppm) | Fluoride Source (ppm) | Plaque Mean Fluoride Uptake ± (SEM) | Statistic |
|---|---|---|---|---|---|---|---|---|
| Ex 2 | 9.5 | Nil | 6000 | 304 | 1244 | 1450 total fluoride (1.1 wt % Na-MFP) | 417 | B |
| Ex 3 | 8.8 | Sorbitol (17 wt %) | 4130 | 189 | 837 | 1450 total fluoride (1.1 wt % Na-MFP) | 74 | D |
| A[1] | 8 | Nil | N/A | 1450 | — | 1450 total fluoride (0.32 wt % NaF) | 97 | D |
| B[2] | 8 | Nil | N/A | 2800 | — | 2800 total fluoride (0.62 wt % NaF) | 200 | C |
| C[3] | 8.6 | Glycerin (~20 wt %) | 4500 | 117 | 823 | 1450 total fluoride (0.76 wt % Na-MFP, 0.1 wt % Na—F) | 90 | D |
| D[4] | 8.8 | Glycerin (~20 wt %) Sorbitol (~10 wt %) | 6200 | 131 | 1086 | 1450 total fluoride (1.1 wt % Na-MFP) | 68 | D |

[1]Control A is provided in Table 1.
[2]Control B is provided in Table 1.
[3]Control C product is COLGATE Maxima Protection Anticaries, Lot No.: EXP1213(L)1364MX1124, having about 25 wt % water.
[4]Control D product is COLGATE Maxima Protection Anticaries, Lot No.: EXP02152055BR12JH, having about 25 wt % water.

Table 2 summarizes the results obtained from measuring the Mean Fluoride Uptake in plaque across the identified examples and controls. The first column identifies the product name Example 1 is an inventive dentifrice composition having a dual fluoride source, whereas examples 2 and 3 are comparative compositions (not within the scope of the present invention). Examples 2 and 3 have a single fluoride source (namely 1.1 wt % Na-MFP), and example 3 further has a polyol humectant, namely sorbitol (17 wt %). Controls A and B are also provided, with compositional components provided in Table 1 above. Additional controls C and D are provided in Table 2 which are commercialized products. Notably, control D has a single fluoride source with Na-MFP where as control C is dual fluoride source having both Na-MFP and Na—F at formulation levels the same as the inventive composition (0.76 wt % Na-MFP, and 0.1 wt % Na—F). However, both control C and control D have relatively high levels of glycerin, or glycerin and sorbitol, respectively.

The second column identifies the pH of the composition. All samples are pH basic, between pH 8 to 9.5. The third column identifies the humectant type and weight percentage (if any). Examples 1, 2 and Controls A, and B do not contain any humectants. The fourth column identifies the amount of MFP ion in the dentifrice composition, if any, on a part per million (ppm) basis. The fifth column identifies the amount of fluoride ion in the dentifrice composition, if any, on a ppm basis. The sixth column identifies the soluble fluoride on a ppm basis. The seventh column identifies the fluoride source in the compositions as well as the total fluoride concentration (parts per million (ppm)). The weight percentage of fluoride source in the commercial product can be inferred from the ppm levels indicated on the packaging. Notably, inventive example 1 and Control C are dual fluoride source compositions. Turning to column eight, the Mean Fluoride Uptake is assessed per the method as previously described and the Standard Error of Mean (SEM). Lastly, the final column labeled as "Statistic" designates whether any tested product is A, B, C, or D (with A as the highest performing sample and D as the lowest performing sample with respect to fluoride Uptake). A Gate-keeper Tukey statistical pair-comparison analysis method is used to group treatments and assess the relevant Statistic.

In table 2, inventive example 1 demonstrates the highest level of Mean Fluoride Uptake at 1141. A "Statistic" of "A" is represented for the inventive composition, wherein as the comparative, control, and commercialized compositions all had a lower Mean Fluoride Uptake value and a "Statistic" lower than A. Notably, a key difference between inventive example 1 vs. comparative examples 2 and 3, is that example 1 contains a dual fluoride source (and not a single one). Moreover, example 3 contains the polyol humectant sorbitol which may have contributed to the poorest outcome between the three examples. Without wishing to be bound by theory, the presence of humectant inhibited Mean Fluoride Uptake. Control C did not perform as well as inventive example 1 despite having a dual fluoride source. Without wishing to be bound by theory, the presence of humectant may be one factor that led to better results by the inventive formulation. The inventive formulation also differs from this commercial product by at least having a higher level of water and a higher pH.

The potential negative effect of humectant on soluble fluoride levels (column 6) is likely best illustrated by comparing examples 1 and 2 that do not have humectant, and that of example 3 having humectant sorbitol. Examples 1 and 2 have these levels at 1246 and 1244, respectively, while Example 3 is at 837. However, as previously discussed, inventive example 1 has a higher Mean Fluoride Uptake than comparative example 2.

One aspect of the invention provides for a use of any dentifrice composition according to the present invention to provide a Mean Fluoride Uptake (as described herein) greater than 500 ppm, preferably greater than 700 ppm, more preferably greater than 900 ppm, yet still more preferably greater than 1,100 ppm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dentifrice composition comprising:
   (a) 45% to 75%, by weight of the composition, of water;
   (b) 25% to 50%, by weight of the composition, of a calcium-containing abrasive;
   (c) 0.0025% to 2%, by weight of the composition, of sodium monofluorophosphate;
   (d) 0.0025% to 2%, by weight of the composition, of sodium fluoride; and
   (e) a thickening system, wherein the thickening system is selected from the group consisting of a thickening polymer, a thickening silica, or combinations thereof; wherein the thickening polymer selected from the group consisting of carboxymethyl cellulose, a linear sulfated polysaccharide, a natural gum, and combinations thereof, the composition is free of a humectant, and the composition has a pH greater than 7.8.

2. The dentifrice composition of claim 1, wherein the composition comprises from 0.2% to 1.5%, by weight of the composition, of sodium monofluorophosphate.

3. The dentifrice composition of claim 2, wherein the composition comprises from 0.5% to 1%, by weight of the composition, of sodium monofluorophosphate.

4. The dentifrice composition of claim 1, wherein the composition comprises from 0.01% to 0.3%, by weight of the composition, of sodium fluoride.

5. The dentifrice composition of claim 1, wherein the composition comprises from 0.015% to 0.15%, by weight of the composition, of sodium fluoride.

6. The dentifrice composition of claim 1, comprising from 27% to 37%, by weight of the composition, calcium-containing abrasive wherein the calcium-containing abrasive comprises calcium carbonate.

7. The dentifrice composition of claim 1, wherein the pH is greater than pH 8.5.

8. The dentifrice composition of claim 7, wherein the pH is from 9.0 to pH 10.5.

9. The dentifrice composition of claim 1, wherein the composition comprises from 50% to 60%, by weight of the composition, of water.

10. The dentifrice composition of claim 1 wherein the composition comprises from 0% to 5%, by weight of the composition, of a silicate.

11. The dentifrice composition of claim 10, wherein the composition is free of silicate.

12. The dentifrice composition of claim 1 wherein the humectant comprises glycerin, sorbitol, or combinations thereof.

13. The dentifrice composition of claim 1, wherein the composition further comprises from 0.1% to 12%, by weight of the composition, of an anionic surfactant.

14. The dentifrice composition of claim 13, wherein the anionic surfactant comprises sodium lauryl sulfate.

15. The dentifrice composition according to claim 1, wherein the thickening polymer comprises from 0.01% to 3%, by weight of the composition, carboxymethyl cellulose.

16. The dentifrice composition according to claim 1, wherein the thickening polymer comprises from 0.01% to 2.5%, by weight of the composition, linear sulfated polysaccharide comprising carrageenan.

* * * * *